United States Patent [19]
Harrison

[11] Patent Number: 5,828,273
[45] Date of Patent: Oct. 27, 1998

[54] PHASE SPLITTER FOR HIGH DATA RATE COMMUNICATION

[75] Inventor: Daniel David Harrison, Delanson, N.Y.

[73] Assignee: General Electric Company, Schenectady, N.Y.

[21] Appl. No.: 667,912

[22] Filed: Jun. 20, 1996

Related U.S. Application Data

[62] Division of Ser. No. 407,089, Mar. 20, 1995, Pat. No. 5,579,357.
[51] Int. Cl.⁶ ............................................... H01P 5/12
[52] U.S. Cl. ........................ 333/127; 333/128; 333/26; 333/246
[58] Field of Search .................... 333/120, 124, 333/127, 128, 136, 26, 156, 160, 161

[56] References Cited

U.S. PATENT DOCUMENTS

| | | | |
|---|---|---|---|
| 3,314,025 | 4/1967 | Buschbeck | 333/26 X |
| 4,023,123 | 5/1977 | Reindel | 333/120 X |
| 4,460,877 | 7/1984 | Sterns | 333/26 |

*Primary Examiner*—Paul Gensler
*Attorney, Agent, or Firm*—Marvin Snyder

[57] ABSTRACT

A phase splitter includes an input port coupled to receive a modulated carrier having a relatively wide bandwidth and has first and second output ports for supplying, respectively, first and second modulated carrier constituents having a uniform phase angle differential, such as 180°, between one another while maintaining a uniform amplitude over the bandwidth for the modulated carrier. A transmission line comprised of one or more individual segments includes first and second conductors respectively coupled to the output ports of the phase splitter to receive the first and second modulated carrier constituents from the phase splitter. A coupler is positioned sufficiently near the transmission line to receive the first and second modulated carrier constituents being applied to any of the individual segments.

20 Claims, 6 Drawing Sheets fig. 1 fig. 2 fig. 3 fig. 4 fig. 5 fig. 7

PHASE SPLITTER FOR HIGH DATA RATE COMMUNICATION

This application is a division of application Ser. No. 08/407,089, filed Mar. 20, 1995, now U.S. Pat. No. 5,579,357.

RELATED APPLICATIONS

This application is related to patent application Ser. No. 08/407,149, entitled "Transmission line Using a Power Combiner For High Data Rate Communication In a Computerized Tomography System", filed Mar. 20, 1995, now U.S. Pat. No. 5,600,697, issued Feb. 4, 1997, assigned to the same assignee of the present invention and herein incorporated by reference.

BACKGROUND OF THE INVENTION

The field of the present invention is generally related to computerized tomography (CT) and, particularly, to a transmission line using an accurate, wideband phase splitter for high data rate communication in a CT system.

CT systems typically employ a rotating frame or gantry to obtain multiple x-ray images, or views, at different rotational angles. Each set of images is referred to in the art as a "slice". A patient or inanimate object is generally positioned in a central opening of the rotating frame on a table which is movable axially, thus enabling respective slices to be obtained at multiple axial positions as well. Each of the slices obtained is then processed in a computer according to predetermined algorithms to produce enhanced images for diagnostic or inspection purposes.

The rotating frame includes an x-ray source, a detector array and electronics necessary to generate image data for each view. A set of stationary electronics is employed for processing raw image data into the enhanced form. Thus, it is necessary to provide for communication of the image data between the rotating frame and a stationary frame of the CT system.

The data rate for communication between the stationary and rotating frames is an important factor because it is desirable to obtain the desired views as fast as possible to reduce patient discomfort and/or to maximize equipment utilization. In current CT systems, a single view typically comprises about 800 detector channels with a 16 representation for each individual detector channel output (i.e., 12.8 Kbits per view) and is typically repeated 1,000 times per second, yielding a net data rate requirement of approximately 13 Megabits per second (Mbit/sec) for image data alone. Future CT systems capable of simultaneously constructing multiple image slices by employing four, eight, or sixteen times as many detector channels will increase the data rate requirement to beyond 150 Mbit/sec for image data alone.

Prior CT systems have employed brushes and slip rings for electrically linking the rotating frame to the stationary frame. However, in general, CT systems utilizing brushes and slip rings for communications have generally suffered from significant limitations in the data rates which can be achieved. This is due to the substantial time required to propagate the signals around the circular slip rings. At the desired data rates, the electrical path length around the rings is an appreciable fraction of a bit period, so that electromagnetic waves propagating around the rings in opposite directions may arrive at a reception point at substantially different times in a bit period, causing garbled reception.

U.S. Pat. No. 5,208,581 issued to A. K. Collins, assigned to the assignee of the present invention and herein incorporated by reference, teaches another type of gantry in which brushes and slip rings are employed for communication. Although the design of Collins provides relatively high speed communication between the stationary and rotating frames, the fact remains that the use of contacting brushes and rings inherently carries certain disadvantages. For example, the mechanical contact between the brushes and rings causes wear which requires such brushes and rings to be periodically replaced in order to maintain reliable communication. Furthermore, the slip-ring design of Collins does not support the higher data rates needed for multiple-slice CT systems.

Other CT systems have employed an optical data link for communication between the stationary and rotating frames. Although an optical data link design avoids typical drawbacks of slip rings and brushes, such optical design requires optics which must be fabricated under tight specifications and which in operation require substantial spatial alignment in order to achieve reliable optical coupling along the relatively long circumference of the rotating frame. This leads to high costs and, thus, it is desirable to provide in a CT system an improved communication link which at a low cost provides reliable high data rate communication between the stationary and rotating frames of the CT system.

It is further desirable to provide a communication link between the stationary frame and the rotating frame which is robust with respect to electromagnetic radiation interference such as is typically produced in a hospital environment by cellular telephones, defibrillating devices, surgical saws and even electrical noise produced by any given CT system. Furthermore, it is also desirable to reduce the level of electromagnetic energy which is radiated from such communication link in order to comply with governmental regulations such as regulations imposed by the Federal Communications Commission and/or foreign governments. As disclosed in U.S. patent application Ser. No. 08/307,120, a transmission line and a coupler or probe provide means for implementing such high data rate communication link. As further disclosed in U.S. patent application Ser. No. 08/307,130, a U-shaped structure is effectively employed for substantially reducing electromagnetic radiation from the transmission line while providing a passage which allows for the coupler to readily access the transmission line. Although such U-shaped structure effectively shields the transmission line, it is desirable to reduce electromagnetic radiation which escapes or leaks around the coupler. It is also desirable to reduce sensitivity of the coupler to externally produced electromagnetic energy which can interfere with coupler operation.

SUMMARY OF THE INVENTION

Generally speaking, the present invention fulfills the foregoing needs by providing in a computerized tomography (CT) system having a stationary frame and a generally annular rotating frame, an apparatus comprising a phase splitter having an input port coupled to receive a modulated carrier having a predetermined bandwidth. The phase splitter has first and second output ports for supplying, respectively, first and second modulated carrier constituents having a substantially uniform phase angle differential, such as about 180°, between one another while maintaining a substantially uniform amplitude over the bandwidth for the modulated carrier. A transmission line is attached to the rotating frame and is positioned substantially around the annular rotating frame. The transmission line comprises one or more individual segments having first and second conductors respectively coupled to the output ports of the phase splitter to receive the first and second modulated carrier constituents from the phase splitter. A coupler is attached to the stationary frame and is positioned sufficiently near the transmission line for establishing radio coupling therebetween so as to receive the first and second modulated carrier constituents being applied to any individual segment.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like numbers represent like parts throughout the drawings, and in which:

DETAILED DESCRIPTION OF THE INVENTION

Figure 1:
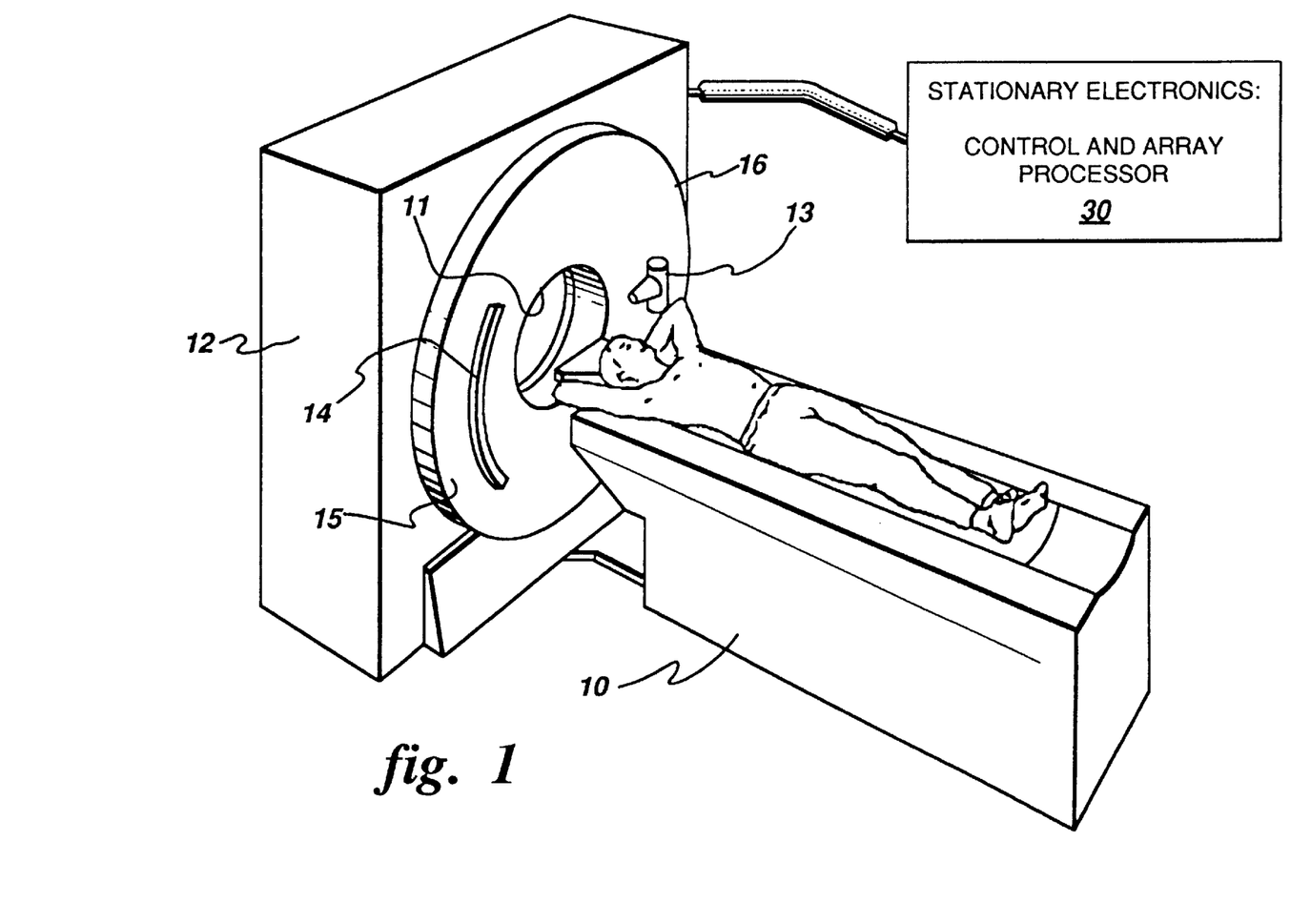
FIG. 1 is a perspective view of a CT system which employs the present invention.

As shown in FIG. 1, a CT system used to produce images of at least a region of interest of the human anatomy has a patient table 10 which can be positioned within the aperture 11 of a generally annular rotating frame or gantry 15 having a predetermined circumference, e.g., outer circumference 16. A stationary frame 12 is conveniently employed to support rotating frame 15. A source of imaging energy 13 which preferably produces highly collimated x-rays is mounted on the rotating frame to one side of its aperture 11, and a detector array 14 is mounted to the other side of the aperture. The rotating frame, together with x-ray source 13 and detector array 14, is revolved about the aperture during a scan of the patient to obtain x-ray attenuation measurements from many different angles through a range of at least 180° of revolution. Detector array 14 may comprise multiple rows each having about 800 detector channels along its length. The individual output of each channel in detector array 14 is connected to a data acquisition system, DAS (not shown). When sampled, each channel output is converted by the DAS to, for example, a 16 digital value representing X-ray intensity.

The rotating frame further includes additional onboard electronics (not shown) which rotates along with rotating frame 15. The onboard electronics is essentially a slave to stationary electronics systems 30 which is located off rotating frame 15. Stationary electronics systems 30 is a computer-based system for issuing commands to the onboard electronics on rotating frame 15 and for receiving the resulting image data, via suitable electrical leads from stationary frame 12, to perform processing of the received image data.

The present invention is directed to apparatus for high data rate communication between the rotating frame and the stationary frame through the use of a transmission line that is differentially driven by an accurate, wideband phase splitter. The transmission line is, in turn, noncontactively coupled to a probe or coupler. This noncontactive coupling advantageously avoids the use of slip rings and brushes and allows for continuous rotation of rotating frame 15. As discussed above, multiple-slice CT systems require high data rate communication. The present invention advantageously allows for such high data rate communication, (e.g., exceeding 150 Mbits/sec) without the use of brushes and slip rings or without the use of costly optical devices. Further, the present invention allows for reliable and cost effective high data rate communication notwithstanding the relatively long circumference (approximately 13 ft) of the rotating frame.

In the discussion which follows, it is assumed that all of the communication between rotating frame 15 and stationary frame 12 has been serialized, i.e., converted from parallel to serial data for transmission and vice versa on reception, employing well known multiplexing techniques. This is done so that only a single bit stream need be transmitted, although it should be apparent to those skilled in the art that multiple parallel paths according to the present invention could be employed. In each case, multilevel or multiphase encoding techniques can be employed to further increase the maximum data rate available.

Figure 2:
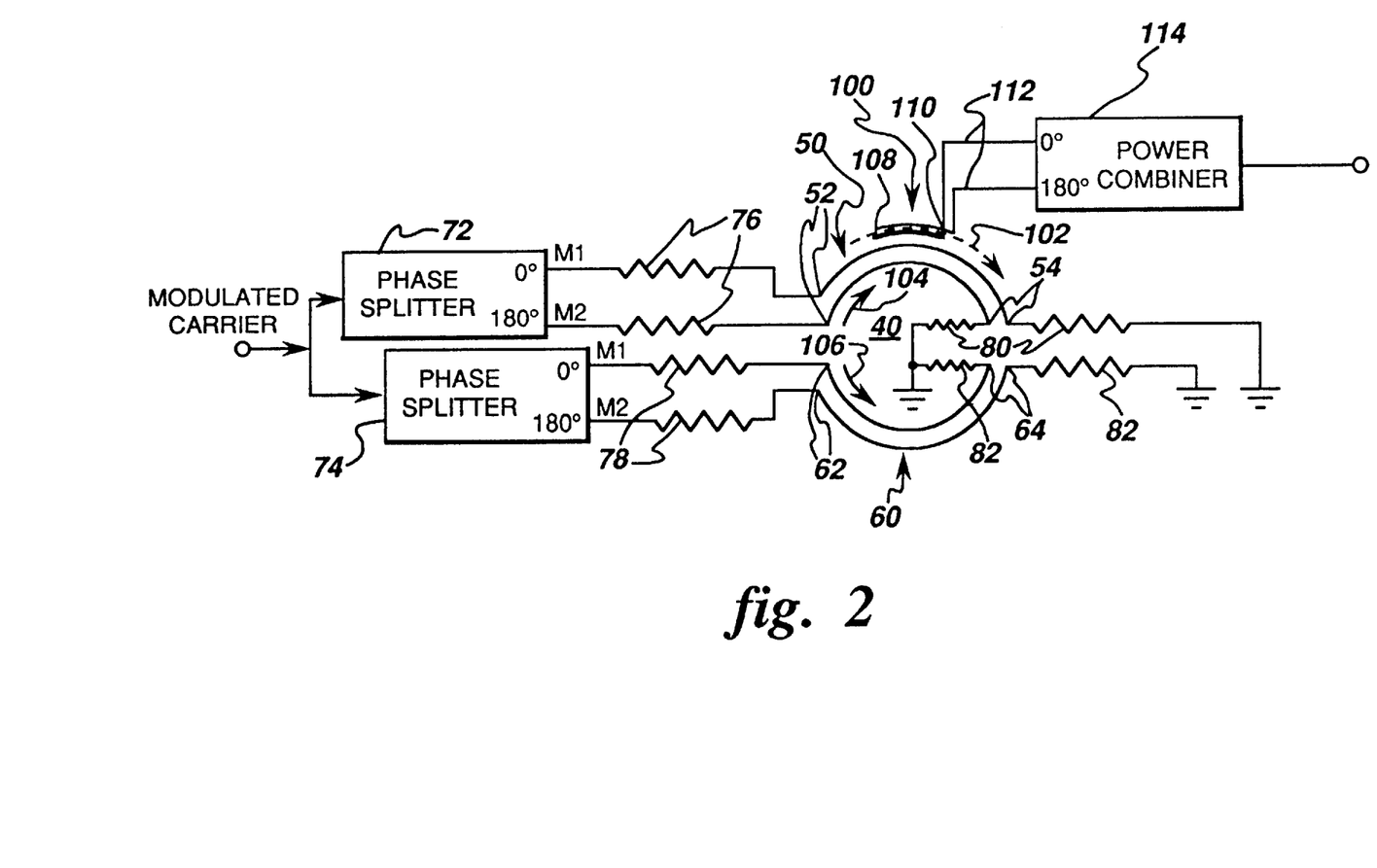
FIG. 2 is an exemplary schematic representation of an apparatus employing a coupler electromagnetically coupled to a transmission line having individual segments driven by a respective phase splitter in accordance with the present invention.
Figure 3:
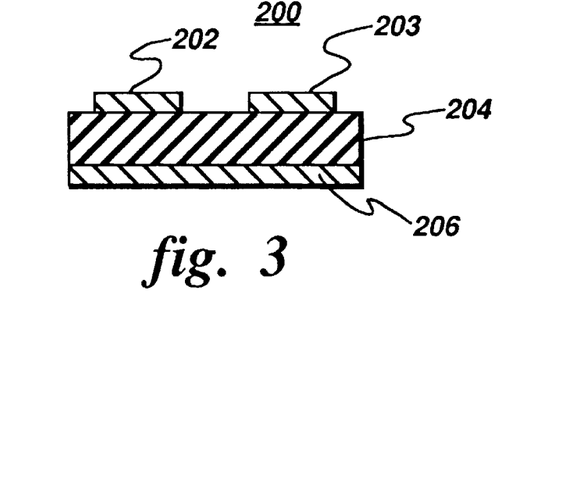
FIG. 3 is a cross section of a microstrip which can be utilized for the transmission line and/or coupler in respective exemplary embodiments for the apparatus of FIG. 2.

As shown in FIG. 2, a transmission line 40 is attached to rotating frame 15 (FIG. 1) and is positioned substantially around the rotating frame, for example, around the circumference of the rotating frame. Similarly, the transmission line can be conveniently affixed to the annulus of the rotating frame, i.e., the surface bounded by the concentric circles in the rotating frame; for example, the concentric circle which defines aperture 11 and the larger concentric circle which has circumference 16. Further, it will be appreciated that the present invention need not be limited to circular geometric arrangements since geometric arrangements other than circular can equally benefit from the present invention. Transmission line 40 comprises one or more segments, such as individual segments 50 and 60 each having a respective first end 52 and 62 and a respective second end 54 and 64. In FIG. 2, each respective individual segment is represented by twin lines since, as best seen in FIG. 3, each of the individual segments includes first and second signal conductors carrying respective signals being substantially 180° out-of-phase with respect to one another, that is, each transmission line segment is differentially driven by a respective phase splitter, such as phase splitters 72 and 74. Although two phase splitters are shown in FIG. 2, it will be appreciated that the output signals from a single phase splitter could be readily split and amplified for effectively driving individual transmission line segments 50 and 60; thus, one need not use a separate phase splitter for driving each respective one of the individual segments. For example, one respective first end of segments 50 and 60 could be readily connected in parallel to receive the in-phase output signal of a single phase splitter while the other respective first end of segments 50 and 60 could be connected in parallel to receive the out-of-phase output signal of the single phase splitter and thus, in this example, only a single phase splitter would be needed for driving segments 50 and 60. Preferably, each individual segment 50 and 60 has a respective electrical length chosen so that a modulated signal applied at each respective first end 52 and 62 has a predetermined time-delay upon arrival at each respective second end 54 and 64. It will be appreciated that if the respective electrical lengths for segments 50 and 60 are substantially similar to one another, the above-described segment arrangement results in the modulated signal arriving at each respective second end with a substantially similar time delay relative to one another.

As shown in FIG. 2, a modulated carrier is applied to the respective input ports of phase splitters 72 and 74. The modulated carrier typically has a relatively wide bandwidth, such as from 100 MHz to over 1 GHz. The modulated carrier can be conveniently generated by the onboard electronics on rotating frame 15 employing any of a number of readily available modulation techniques, such as pulse amplitude modulation, frequency-shift keying and the like. As shown in FIG. 2, phase splitters 72 and 74 have respective output ports for supplying respective output signals, such as respective first and second modulated carrier constituents $M_1$ and $M_2$ having a substantially uniform phase angle differential, such as 180°, between one another while maintaining a substantially uniform amplitude over the bandwidth of the modulated carrier. As suggested above, each segment receives the respective first and second modulated carrier constituents which are substantially 180° out-of-phase with respect to one another. Each respective phase splitter output port can be optionally connected to matching resistors 76 and 78 having a predetermined resistance value selected to match the impedance characteristics of the respective transmission line segments. Similarly, each respective second end 54 and 64 is respectively connected to termination resistors 80 and 82 having a predetermined resistance value chosen to minimize reflection of energy in individual transmission line segments 50 and 60. Other arrangements may be employed which although having differences in time delay between individual segments, such time-delay differences can be tolerated depending on the specific application. For example, phase splitter 74 and matching resistors 78 could be respectively connected to each second end 64 in lieu of each first end 62 and termination resistors 82 respectively connected to each first end 62 in lieu of each second end 64. In this case although a predetermined time delay would exist between the individual segments, such time delay could be acceptable in certain applications.

Individual segments 50 and 60 are preferably arranged so that respective first ends of any two consecutive segments are substantially adjacent to one another and respective second ends of any two consecutive segments are substantially adjacent to one another. The gap size between any two consecutive segments should be small relative to carrier wavelength. For example, about ⅛ in. for a 750 MHz carrier. This arrangement conveniently allows for avoiding time-delay discontinuities between any of the respective individual segments encircling the rotating frame. This also allows for effective coupling operation between the transmission line and the coupler at all rotation angles. As shown in FIG. 2, each of the two individual segments 50 and 60 can be designed to subtend a respective angle of about 180° around the circumference of the rotating frame. In general, it will be appreciated that a number of N individual segments each respectively subtending an angle of about 360°/N around the circumference of the rotating frame wherein N is a predetermined even number will be equally effective in alternative embodiments of the present invention since the modulated differential signal (i.e., the net result of the first and second modulated carrier constituents being substantially 180° out-of-phase with respect to one another) in each case is available for reception anywhere along the circumference of the rotating frame including any gaps between any of the N individual segments. As suggested above, there may be applications which can tolerate a predetermined time delay between the individual segments. In this case, the N number of individual segments need not be limited to an even number since a predetermined odd number of individual segments could be effectively utilized for applications which tolerate such predetermined time delay. The foregoing construction for the individual segments assumes that each segment is made up of a material having a substantially similar dielectric constant. However, it will be apparent that segment materials having predetermined different dielectric constants can also be conveniently employed. In this case, the angle subtended by each respective individual segment need not be identical to each other.

The apparatus of the present invention further comprises a coupler 100 attached to stationary frame 12 (FIG. 1) and being positioned sufficiently near the differentially driven transmission line for establishing radio coupling therebetween in order to receive the first and second modulated carrier constituents being applied to the individual segments. As used herein the expression "radio coupling" refers to noncontactive transfer of energy by electromagnetic radiation at radio frequencies.

It will be appreciated that coupler 100 has a predetermined length dimension along a coupler axis 102 which, for example, can be substantially parallel relative to individual segments 50 and 60. The coupler length dimension is conveniently chosen to be sufficiently short to substantially avoid frequency-dependent directional coupling effects, and to be sufficiently long to avoid substantial signal reduction in coupler 100 whenever the coupler passes about any gap between respective ones of the individual segments. As indicated by arrows 104 and 106, the respective modulated carrier constituents applied to respective segments 50 and 60 propagate in opposite directions and thus to avoid blind spots near any of the gaps, coupler 100 preferably has a first end 110 directly connected to output port means, such as a coaxial line pair 112 or other suitably shielded electrical conductor pair, and has a second end 108 which is substantially free of any termination impedance, i.e., termination resistors. In this manner, each modulated carrier constituent received by coupler 100 passes to coaxial line pair 112 independently of the propagation direction of the received modulated carrier constituents, i.e., independently of the propagation direction of the respective electromagnetic waves traveling in individual segments 50 and 60. For instance, waves arriving at second end 108 readily propagate toward the first end and from there to coaxial line pair 112, whereas waves arriving at first end 110 are eventually reflected back from the unterminated second end 108 toward the first end and from there to coaxial line pair 112. In each case, coupler 100 advantageously allows for noncontactively extracting the respective 180° out-of-phase modulated carrier constituents propagating in the transmission line along the full circumference of the rotating frame. A power combiner 114 recombines into a single modulated carrier the first and second modulated carrier constituents being supplied by coupler 100. For additional details about the power combiner the reader is referred to U.S. Pat. No. 5,600,697, issued Feb. 4, 1997, entitled "Transmission Line Using a Power Combiner For High Data Rate Communication in a Computerized Tomography System", by D. D. Harrison, assigned to the same assignee of the present invention and herein incorporated by reference. As will be appreciated by those skilled in the art, the length dimension of the coupler can vary depending on the specific value of the carrier frequency being utilized for the modulated signal. By way of example and not of limitation, the coupler length dimension can be chosen in the range of $\lambda/4$ to $\lambda/8$ wherein $\lambda$ represents the wavelength of the carrier in the transmission line material. Other configurations for the coupler will be readily apparent to those skilled in the art.

FIG. 3 illustrates a cross section of a substantially planar transmission line which can be effectively used both for the differentially driven transmission line segments and for the coupler. For example, FIG. 3 shows a microstrip 200 wherein substantially parallel first and second conductors 202 and 203 and a ground plane 206 are separated from one another by a suitable dielectric material 204. It will be appreciated that such substantially planar transmission line can be readily fabricated employing well known printed circuit techniques which allow for substantial savings in cost as compared to an optical data link. Similarly, a stripline transmission line wherein the first and second conductors are "sandwiched" in a respective dielectric material between two ground planes can be alternatively employed both for the transmission line segments and for the coupler. Furthermore, the coupler need not consist of a microstrip or a stripline transmission line. A suitable conductor, such as a short piece of twin wires, aligned substantially parallel to the driven transmission line, will also work effectively.

Figure 4:
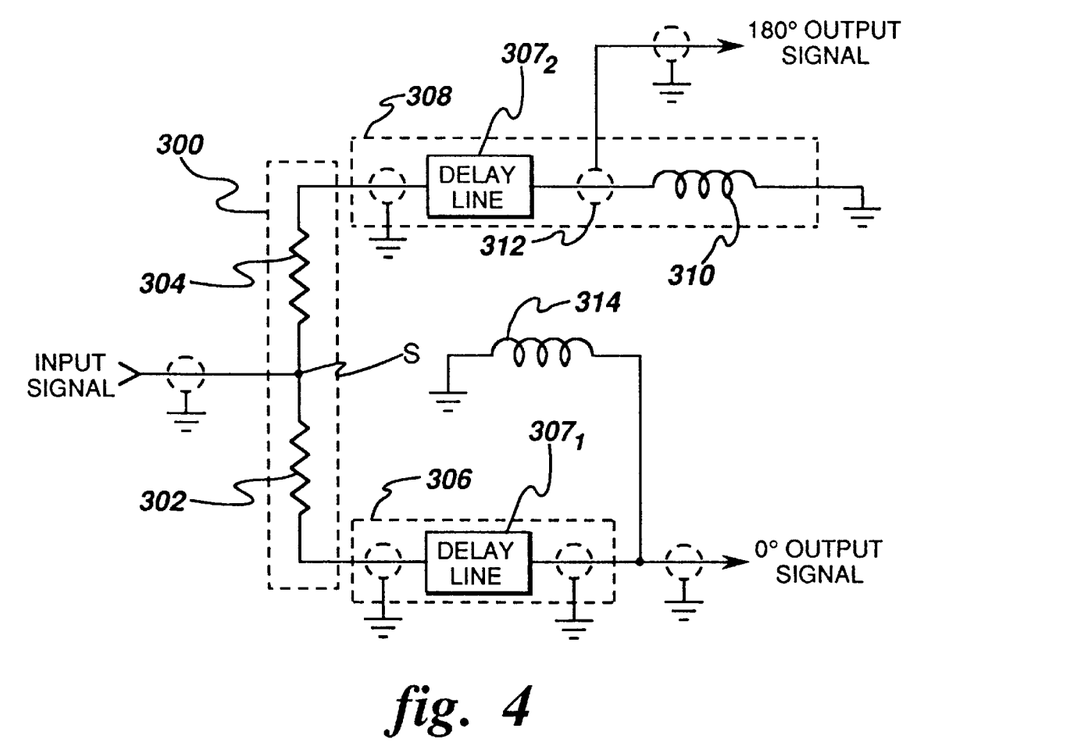
FIG. 4 is a simplified circuit model schematic for the phase splitter in accordance with the present invention.

FIG. 4 shows a simplified circuit model schematic for an accurate, wideband phase splitter, such as either of phase splitters 72 or 74, used for differentially driving transmission line 40 (FIG. 2). As shown in FIG. 4, the phase splitter comprises a dividing network 300 that can optionally include first and second matching resistors 302 and 304 coupled in parallel to the input port of the phase splitter. Matching resistors 302 and 304 are optionally employed in dividing network 300 being that, depending upon any specific implementation for the phase splitter, such matching resistors 302 and 304 can be readily eliminated. A first transmission line 306, schematically represented as a delay line $307_1$ is coupled between first resistor 302 and the first output port of the phase splitter for supplying a respective output signal having a phase angle substantially in-phase with respect to the modulated carrier received at the input port of the phase splitter. As will be understood by those skilled in the art, transmission line 306 introduces a predetermined time delay to any signal propagating therethrough depending upon the electrical length of transmission line 306 and hence the representation of transmission line 306 as a delay line. The output signal supplied by first transmission line 306 is a delayed version of the modulated carrier input and constitutes the first modulated carrier constituent supplied by the phase splitter.

In contrast to first transmission line 306, which as suggested above simply introduces the predetermined time delay, without any phase shifting, to its respective output signal, a second transmission line 308 is designed to provide a predetermined level of inductance between second resistor 304 and a predetermined electrical ground. Thus, second transmission line 308 is schematically represented as a delay line $307_2$ in series with an inductor 310, which represents the inductance imparted by transmission line 308 between second resistor 304 and the predetermined electrical ground. Second transmission line 308 includes reversing means 312 coupled to the second output port for supplying a respective output signal having a phase angle substantially 180° out-of-phase with respect to the modulated carrier. The inductance provided by the second transmission line effectively allows reversing means 312 to impart the desired 180° phase change to the output signal from the second transmission line without electrically shorting such output signal. The output signal supplied by second transmission line 308 constitutes the second modulated carrier constituent supplied by the phase shifter. A compensating coil 314 is coupled between the first output port of the phase splitter and the predetermined electrical ground. Compensating coil 314 effectively balances the level of inductance provided by second transmission line 308 so that each of the first and second transmission lines 306 and 308 provide a substantially identical impedance to the first and second modulated carrier constituents respectively propagating therethrough, assuming the first and second output ports are equally terminated.

It will be appreciated that the respective electrical lengths of the various electrical components which make up the phase splitter, such as dividing network 300 and transmission lines 306 and 308, are preferably selected so that signals which respectively propagate from splitting point S to each of the first and second output ports of the phase splitter have a substantially identical time delay relative to one another upon arrival to the first and second output ports of the phase splitter. Thus, assuming dividing network 300 introduces a substantially identical time delay to signals which propagate from splitting point S, then any time delay introduced, respectively, by the first and second transmission lines 306 and 308 should have a substantially identical value to one another. With respect to matching resistors 302 and 304, it will be appreciated that resistors 302 and 304 could be readily eliminated if the impedance values for transmission lines 306 and 308 were suitably chosen to provide any desired impedance matching between the phase splitter and any circuitry connected to the phase splitter, such as the circuitry (not shown) that generates the modulated carrier being supplied to the input port of the phase splitter. For example, if the input port has an input impedance of 50 Ohms, and if each of transmission lines 306 and 308 has a line impedance of 50 Ohms, then each of matching resistors 302 and 304 would require a value of 50 Ohms to achieve substantial impedance matching between the input port of the phase splitter and each of the first and second transmission lines. In the above example, substantial impedance matching could also be achieved by eliminating matching resistors 302 and 304 and choosing each of transmission lines 306 and 308 to have a line impedance of 100 Ohms. Further, in some applications substantially accurate impedance matching, such as described above, may not be necessary being that some applications can readily tolerate a predetermined level of impedance mismatch. Thus, it will be appreciated that any desired impedance matching in the phase splitter can be achieved in many different ways, including even without the use of matching resistors 302 and 304.

Figure 5:
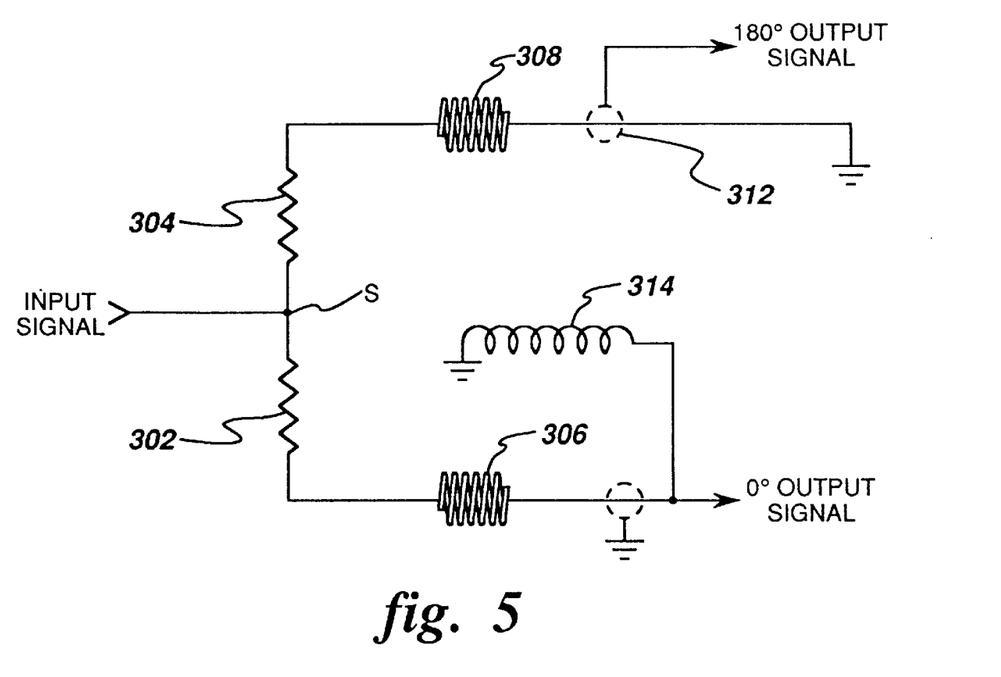
FIG. 5 is a generally schematic representation which includes respective side views of coaxial lines wound to form substantially cylindrical windings in accordance with one exemplary embodiment for the phase splitter of FIG. 4.

FIG. 5 shows one exemplary embodiment for first and second transmission lines 306 and 308. In this embodiment, transmission lines 306 and 308 each comprises a respective coaxial line having a substantially similar electrical length for maintaining the desired phase differential between the first and second modulated carrier constituents. As best shown in FIG. 5, each of the coaxial lines preferably comprises a flexible coaxial line wound to form a substantially cylindrical winding. This configuration, conveniently allows for circuit symmetry and compactness and for relatively low electromagnetic interaction between the first and second transmission lines. In this embodiment, reversing means 312 is conveniently made up by the outer shield and center conductor of the coaxial line for the second transmission line, that is, the center conductor of the coaxial line for the second transmission line is electrically grounded while the outer shield supplies the out-of-phase output signal. Conversely, the outer shield of the first transmission line is electrically grounded while the center conductor supplies the in-phase output signal.

Figure 6A:
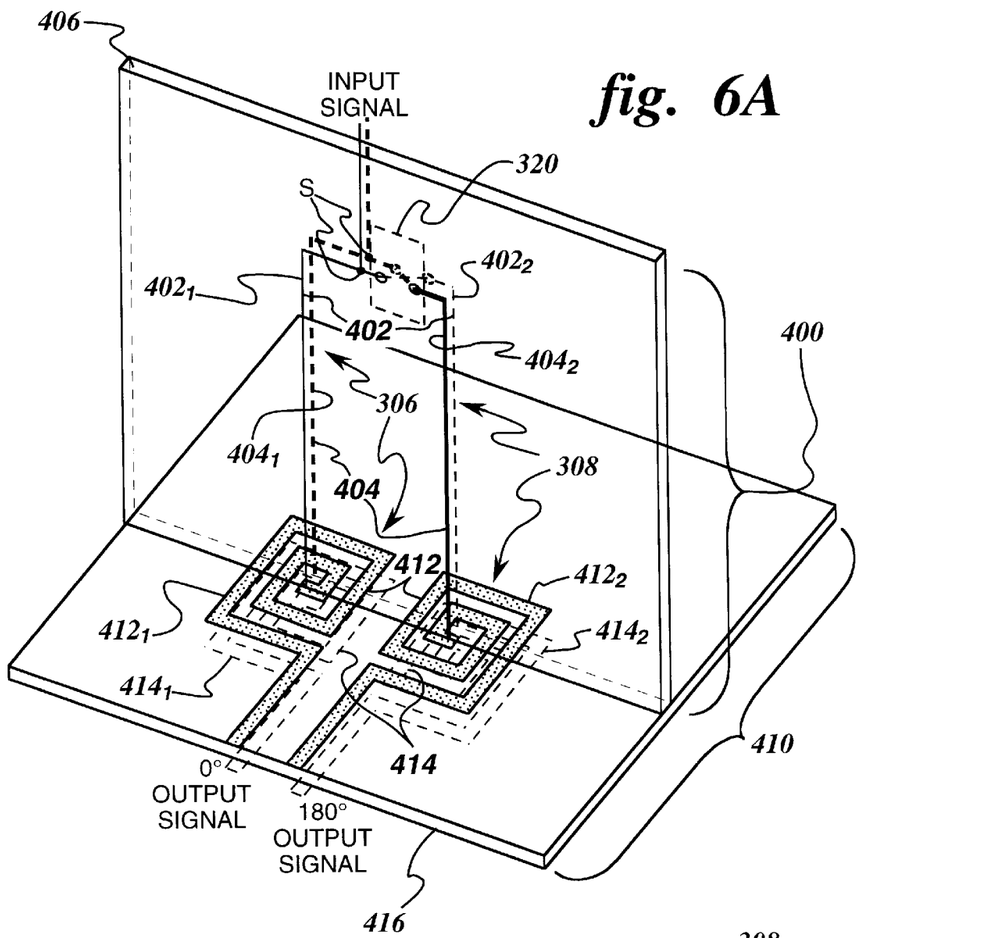
FIG. 6A is a perspective view of two printed circuit stages in accordance with another exemplary embodiment for the phase splitter of FIG. 4, and wherein one of the stages is shown horizontally positioned while the other stage is shown vertically positioned.

FIG. 6A shows another exemplary embodiment for first and second transmission lines 306 and 308 (FIG. 4). In this embodiment, transmission lines 306 and 308 comprise a first printed-circuit stage 400 including for each of the transmission lines a respective pair of substantially corresponding conductive strips, such as strips 402 and 404 disposed on mutually opposite surfaces of a first substrate 406. As shown in FIG. 6A, transmission lines 306 and 308 further comprise a second printed-circuit stage 410 including for each of the transmission lines a respective pair of substantially corresponding coils, such as coils 412 and 414 each respectively coupled, i.e., electrically connected, to a respective one of the conductive strips in the first printed circuit stage. Although conductive strips 402 and 404 are represented in FIG. 6A by thin lines, it will be appreciated that the conductive strips have a width dimension similar to the width dimension for coils 412 and 414. The thin line representation was conveniently chosen for the sake of simplicity of illustration. Further, in FIGS. 6A, 6B and 6C, the subindex numeral assigned to each of corresponding strips 402 and 404 and to each of corresponding coils 412 and 414 conveniently identifies the particular transmission line (of the first and second transmission lines) made-up with such strips and coils. For example, coils $412_1$, and $414_1$, represent the pair of corresponding coils for the first transmission line whereas coils $412_2$ and $414_2$, represent the pair of corresponding coils for the second transmission line. Similarly, strips $402_1$ and $404_1$ represent the pair of corresponding strips for the first transmission line whereas strips $402_2$ and $404_2$ represent the pair of corresponding strips for the second transmission line.

Figure 6B:
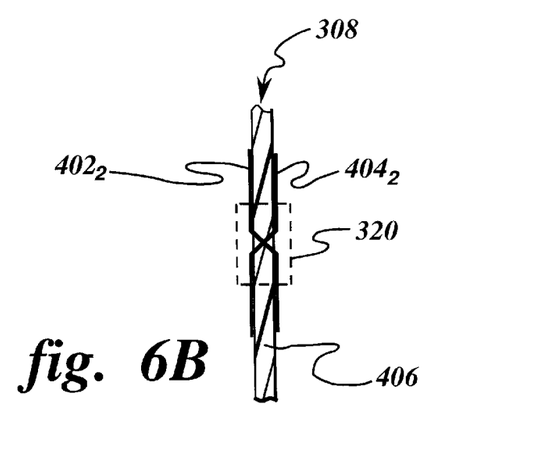
FIG. 6B is a schematic showing a feedthrough connector in the vertical stage shown in FIG. 6A.
Figure 6C:
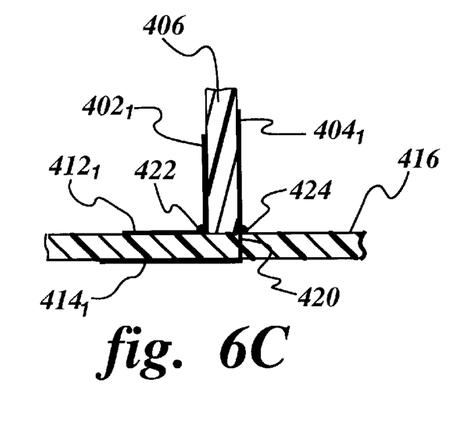
FIG. 6C is a cross-sectional view showing an exemplary electrical connection between the two printed circuit stages of FIG. 6A.

The electrical connection between printed circuit stages 400 and 410 can be made at suitable ends of the conductive strips and coils, as best shown in FIG. 6C for the first transmission line. For example, strip $402_1$ is connected to coil $412_1$ through a respective connecting conductor, such as a conductive joint 422, or a flexible wire and the like. Similarly, strip $404_1$ is connected to coil $414_1$ through a respective connecting conductor, such as a conductive pin 420 electrically connected to strip $404_1$ by way of a suitable conductive joint 424. As shown in FIG. 6C, the connecting end of coil $414_1$ extends beyond the connecting end of coil $412_1$ to take into account the thickness of substrate 406. It will be appreciated that similar electrical connections can be made at suitable ends of the strips and coils for the second transmission line. Similar to conductive strips 402 and 404, coils 412 and 414 are disposed on mutually opposite surfaces of a second substrate 416. Preferably, each of the mutually opposite surfaces on the second substrate is positioned substantially perpendicular relative to the mutually opposite surfaces on the first substrate. This allows for reducing electromagnetic interference between signals propagating in the first and second printed circuit stages. Further, the gap spacing between any two adjacent loops of the concentric loops or turns that respectively make up coils 412 and 414 should preferably be sufficiently wide relative to the loop width for reducing electromagnetic crosstalk therebetween. For example, the gap spacing can be readily selected to be about three times as wide as the loop width. Although FIG. 6A shows coils 412 and 414 as having concentric loops with corners, i.e., generally rectangular loops, it will be appreciated that other geometric configurations will also work equally effective for the coil loops. For example, the coil loops could be made generally circular and the like, in lieu of generally rectangular.

In this embodiment, reversing means 312 (FIG. 4) comprises a feedthrough connector 320, conceptually shown in FIG. 6B. The feedthrough connector is designed to invert signal flow across each respective one of the pair of substantially corresponding strips for the second transmission line. For example, as conceptually shown in FIG. 6B, feedthrough connector 320 allows for inverting signal flow in second transmission line 308 across conductive strips $402_2$ and $404_2$ disposed on the mutually opposite surfaces of substrate 406, that is, the signal carried by strip $402_2$ passes through substrate 406 and continues along the surface situated opposite to the surface where strip $402_2$ was located prior to being spatially inverted or flipped by feedthrough connector 320, while the signal carried by strip $404_2$ passes through substrate 406 and continues along the surface situated opposite to the surface where strip $404_2$ was located prior to being spatially reversed or flipped by feedthrough connector 320. As will be apparent to those skilled in the art, feedthrough connector 320 is designed to avoid electrically shorting out any signals propagating in the respective conductive strips. It will be appreciated that by using printed circuit stages, a phase splitter in accordance with the present invention can be readily fabricated employing well-known printed circuit techniques which allow for substantial savings in cost over other circuit fabrication techniques. Although not explicitly shown in FIG. 6A, it will be appreciated that matching resistors 302 and 304 (FIG. 4) and compensating coil 314 (FIG. 4) can be readily incorporated to the embodiment of FIG. 6 using well-known printed circuit techniques. See for example, a paper by C. Brunetti and R. Curtis, entitled "Printed Circuit Techniques", pp. 121–159, Proceedings of the I.R.E., Waves and Electrons Sections, January, 1948, for an early but comprehensive treatment of various printed circuit techniques. It will also be appreciated that, as suggested above, the respective electrical lengths of transmission lines 306 and 308 are preferably chosen substantially identical to one another for maintaining the desired phase differential between the first and second modulated carrier constituents.

Figure 7:
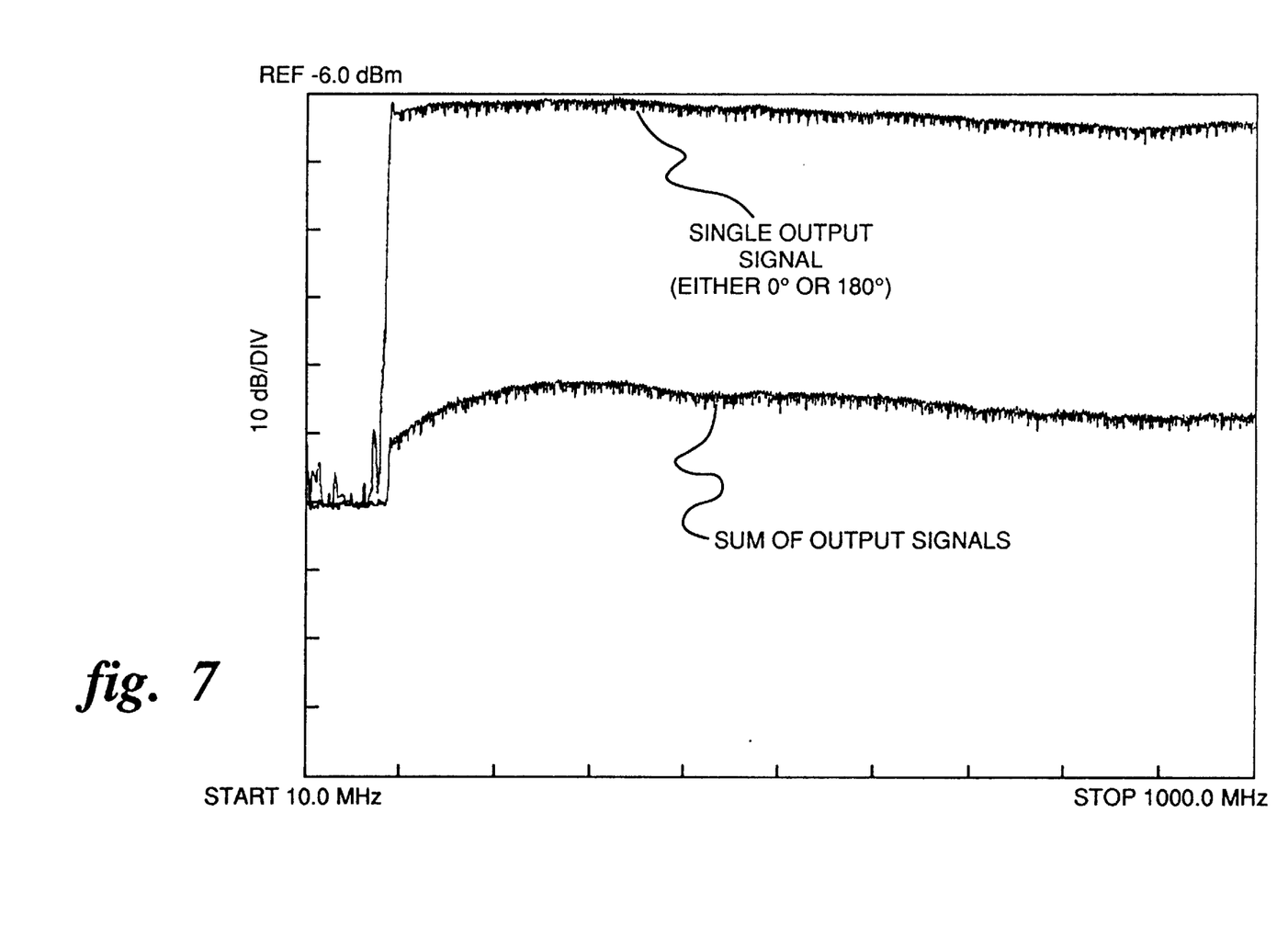
FIG. 7 is a plot showing exemplary output signal characteristics of a phase splitter in accordance with the present invention.

FIG. 7 is a plot showing exemplary output characteristics for a phase splitter in accordance with the present invention. In this example, it can be seen that the phase splitter advantageously provides a substantially uniform 180° phase differential while providing a substantially uniform amplitude over the bandwidth of interest. The plot shown in FIG. 7 assumes a flat amplitude input signal swept from 10 to 1000 MHz. As shown in FIG. 7, the signal labeled "single output signal" represents an exemplary output signal provided by either one of the output ports of the phase splitter while the signal labeled "sum of output signals" represents the sum of the substantially 180° out-of-phase output signals supplied by the phase splitter. As shown in FIG. 7, at least 30 dB of cancellation is obtained in the signal summation, indicating that the output signals from the phase splitter are in fact of substantially equal amplitude and substantially 180° out-of-phase over the bandwidth of interest.

Although various specific constructions have been given for the present invention, it is to be understood that these are for illustrative purposes only. Various modifications and adaptations will be readily apparent to those skilled in the art without departing from the substance or scope of the invention. For example, although the shielded transmission line segments have been described as rotating along with rotating frame or gantry 15 (FIG. 1) and the coupler has been described as attached to stationary frame 12 (FIG. 1), it is equally possible to instead have the shielded transmission line segments stationary and the coupler mounted on the rotating frame, i.e., stationary and rotating mechanical mounting for the coupler and transmission line segments can be readily interchanged with equally effective results. Accordingly, it is intended that the invention be limited only by the spirit and scope of the claims appended hereto.

What is claimed is:

1. A phase splitter having an input port coupled to receive a modulated carrier having a predetermined bandwidth, said phase splitter having first and second output ports for supplying, respectively, first and second modulated carrier constituents having a substantially uniform 180° phase angle differential between one another while maintaining a substantially uniform amplitude over said bandwidth, said phase splitter comprising:

a first transmission line coupled between said input port and said first output port for supplying a respective output signal having a phase angle substantially in-phase with respect to the modulated carrier, the output signal supplied by said first transmission line constituting the first modulated carrier constituent supplied by said phase splitter; and a second transmission line coupled between said input port and an electrical ground, said second transmission line including reversing means coupled to the second output port for supplying a respective output signal having a phase angle substantially 180° out-of-phase with respect to the modulated carrier and providing a predetermined level of inductance that effectively allows said reversing means to impart the substantially 180° phase angle without electrically shorting the output signal supplied by said second transmission line, wherein the output signal supplied by said second transmission line constitutes the second modulated carrier constituent supplied by said phase splitter.

2. The phase splitter of claim 1 further comprising a compensating coil coupled between said first output port and said predetermined electrical ground.

3. The phase splitter of claim 1 wherein said first and second transmission lines each comprises a respective coaxial line having a substantially similar electrical length relative to one another.

4. The phase splitter of claim 3 wherein each of said coaxial lines comprises a flexible coaxial line wound to form a substantially cylindrical winding.

5. The phase splitter of claim 3 wherein said reversing means comprises the outer shield and the center conductor of the coaxial line for said second transmission line, said center conductor being connected to said predetermined electrical ground while said outer shield is connected to the second output port of said phase splitter to supply the second modulated carrier constituent.

6. The phase splitter of claim 1 wherein said first and second transmission lines comprise a first printed-circuit stage including a respective pair of substantially corresponding conductive strips for each of said transmission lines, respective ones of the conductive strip pairs being disposed on mutually opposite surfaces of a first substrate.

7. The phase splitter of claim 6 wherein said first and second transmission lines further comprise a second printed-circuit stage including a respective pair of substantially corresponding coils for each of said transmission lines, each respective one of the coil pairs being coupled to a respective one of the conductive strips in said first stage and being disposed on mutually opposite surfaces of a second substrate.

8. The phase splitter of claim 7 wherein each of said mutually opposite surfaces on said second substrate is positioned substantially perpendicular relative to the mutually opposite surfaces on said first substrate.

9. The phase splitter of claim 6 wherein said reversing means comprises a feedthrough connector adapted to invert signal flow across each respective one of the pair of substantially corresponding strips for said second transmission line.

10. The phase splitter of claim 9 wherein said first and second transmission lines each has a substantially similar electrical length relative to one another.

11. A phase splitter having an input port coupled to receive a modulated carrier having a predetermined bandwidth, said phase splitter having first and second output ports for supplying, respectively, first and second modulated carrier constituents having a substantially uniform 180° phase angle differential between one another while maintaining a substantially uniform amplitude over said bandwidth, said phase splitter comprising:

a dividing network comprising first and second resistors coupled in parallel to said input port;

a first transmission line coupled between said first resistor and said first output port for supplying a respective output signal having a phase angle substantially in-phase with respect to the modulated carrier, the output signal supplied by said first transmission line constituting the first modulated carrier constituent supplied by said phase splitter; and a second transmission line adapted to provide a predetermined level of inductance between said second resistor and a predetermined electrical ground, said second transmission line including reversing means coupled to the second output port for supplying a respective output signal having a phase angle substantially 180° out-of-phase with respect to the modulated carrier, the output signal supplied by said second transmission line constituting the second modulated carrier constituent supplied by said phase splitter.

12. The apparatus of claim 11 further comprising a compensating coil coupled between said first output port and said predetermined electrical ground.

13. The apparatus of claim 11 wherein said first and second transmission lines each comprises a respective coaxial line having a substantially similar electrical length relative to one another.

14. The apparatus of claim 13 wherein each of said coaxial lines comprises a flexible coaxial line wound to form a substantially cylindrical winding.

15. The apparatus of claim 14 wherein said reversing means comprises the outer shield and the center conductor of the coaxial line for said second transmission line, said center conductor being connected to said predetermined electrical ground while said outer shield is connected to the second output port of said phase splitter to supply the second modulated carrier constituent.

16. The apparatus of claim 1 wherein said first and second transmission lines comprise a first printed-circuit stage including a respective pair of substantially corresponding conductive strips for each of said transmission lines, respective ones of the conductive strip pairs being disposed on mutually opposite surfaces of a first substrate.

17. The apparatus of claim 16 wherein said first and second transmission lines further comprise a second printed-circuit stage including a respective pair of substantially corresponding coils for each of said transmission lines, each respective one of the coil pairs being coupled to a respective one of the corresponding conductive strips in said first stage and being disposed on mutually opposite surfaces of a second substrate.

18. The apparatus of claim 17 wherein each of said mutually opposite surfaces on said second substrate is positioned substantially perpendicular relative to the mutually opposite surfaces on said first substrate.

19. The apparatus of claim 16 wherein said reversing means comprises a feedthrough connector adapted to invert signal flow across each respective one of said another pair of substantially corresponding strips for said second transmission line.

20. The apparatus of claim 19 wherein said first and second transmission lines each has a substantially similar electrical length relative to one another.

* * * * *